(12) United States Patent
Schalkhammer

(10) Patent No.: US 8,257,980 B2
(45) Date of Patent: Sep. 4, 2012

(54) SENSORY PIGMENTS USED ON FOOD, PACKAGING, PAPER AND PHARMACEUTICAL AND ELECTRONIC PRODUCTS

(76) Inventor: Thomas Schalkhammer, Kasten (AT)

( * ) Notice: Subject to any disclaimer, the term of this patent is extended or adjusted under 35 U.S.C. 154(b) by 173 days.

(21) Appl. No.: 12/733,476

(22) PCT Filed: Aug. 28, 2008

(86) PCT No.: PCT/AT2008/000303
§ 371 (c)(1),
(2), (4) Date: May 3, 2010

(87) PCT Pub. No.: WO2009/029964
PCT Pub. Date: Mar. 12, 2009

(65) Prior Publication Data
US 2010/0209521 A1    Aug. 19, 2010

(30) Foreign Application Priority Data

Sep. 3, 2007 (AT) .................................. 1372/2007

(51) Int. Cl.
*G01N 21/01* (2006.01)
(52) U.S. Cl. ...................... 436/164; 436/165; 252/408.1
(58) Field of Classification Search .................. 436/164, 436/165; 252/408.1
See application file for complete search history.

(56) References Cited

U.S. PATENT DOCUMENTS 5,008,136 A * 4/1991 Chamberlain ............. 427/388.1
5,254,473 A * 10/1993 Patel ................................ 436/1
6,472,214 B2 * 10/2002 Patel ................................ 436/2
7,343,872 B2 * 3/2008 Taylor et al. .................. 116/216
7,833,438 B2 * 11/2010 Lucht et al. ................ 252/408.1

FOREIGN PATENT DOCUMENTS

EP      0 732 583      9/1996
WO      03/014681      2/2003

OTHER PUBLICATIONS

M. Bauer et al., "Direct Optical Visualization of DNA-DNA Interaction by Nanoparticle-Capture on Resonant PET-Films", Journal of Nanoscience and Nanotechnology, vol. 6, No. 12, pp. 3671-3676, Dec. 1, 2006.
Translation of the International Preliminary Report on Patentability and Written Opinion of the International Searching Authority issued Apr. 15, 2010 in corresponding International (PCT) Application No. PCT/AT2008/000303.

* cited by examiner

*Primary Examiner* — Jill Warden
*Assistant Examiner* — Monique Cole
(74) *Attorney, Agent, or Firm* — Wenderoth, Lind & Ponack, L.L.P.

(57) ABSTRACT

The invention relates to sensory pigments for use in foods, packagings, pharmaceutical products, paper and electronic products. Said pigments are characterized by the fact that a chemically reactive polymer layer that is 5 to 500 nm thick is applied to metallic particles, metal particles or particles containing at least one metal-oxygen compound, said particles being preferably platelet or fiber-shaped, and a layer of chromophore particles that are between 1 and 100 nm in size is applied to the polymer layer, said particles having a color that is visible to the human eye and that changes after contact with an analyte.

32 Claims, 4 Drawing Sheets

Figure 1:
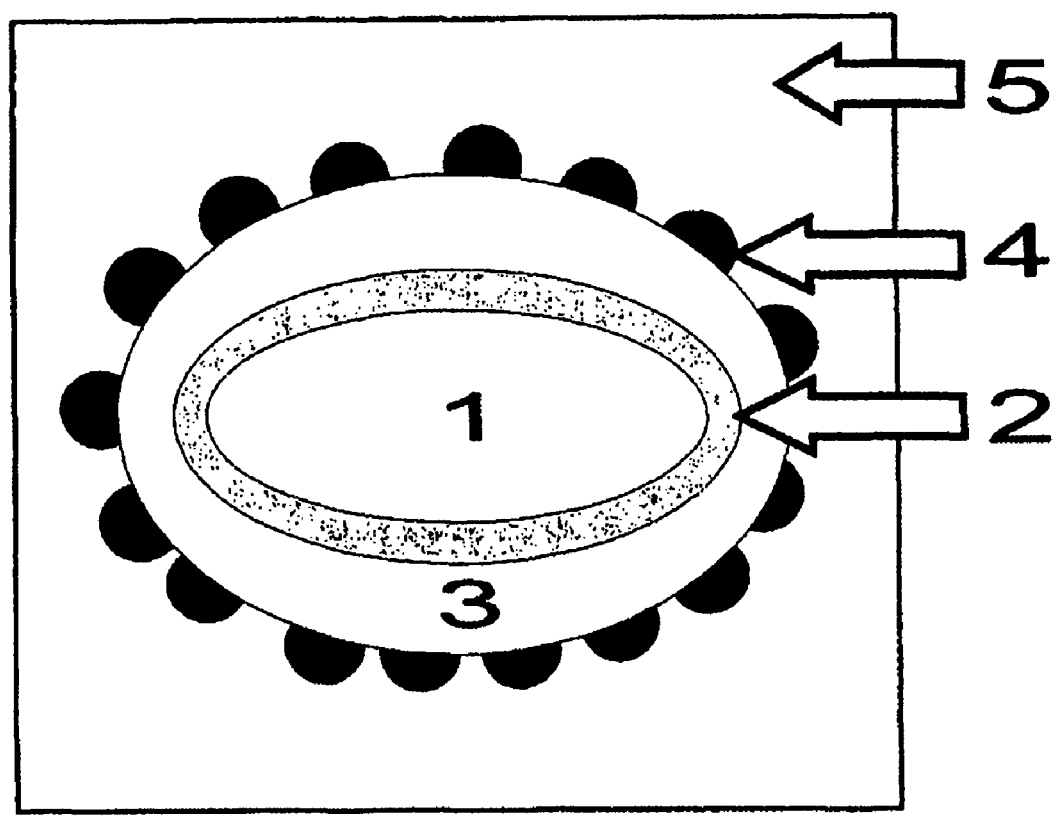

SENSORY PIGMENTS USED ON FOOD, PACKAGING, PAPER AND PHARMACEUTICAL AND ELECTRONIC PRODUCTS

This application is a U.S. national stage of International Application No. PCT/AT2008/000303 filed Aug. 28, 2008.

The invention describes a printable, sprayable or spreadable intelligent nanopigment (used as intelligent ink=nanoink=intelligent nano printing ink) both for smart packaging and for direct use on consumer goods, which, by means of a simple moisture indication, via more complex analytical information about food ingredients, analyzes the food spoilage, both food pathogens and relevant biomedical information and can indicate them visually as a color. Suitable printing techniques for the intelligent nanoinks prepared according to the invention are screen, offset, flexographic or gravure printing and simple printing (e.g. stamp) or writing methods.

The World Health Organization reports that 3.2 million children (under five years) die each year of diseases associated with food poisoning. In the United States and Europe alone, millions of cases of food poisoning occur annually. The integration of sensory labels and labels printed using novel "nanoinks" in and on food packaging materials makes it possible to reduce these numbers significantly.

Use in reactive-smart-intelligent design of products which respond actively to a chemical or physical stimulation with a color change is also expedient and possible, for example a cellphone which changes color when touched.

The multinanolayer-coated pigments according to the invention are applied to disposable packagings, films and labels but also injection molded parts and are active and sensory elements (e.g. for proteins, DNA or other small ligands, such as, for example, water, $CO_2$, organic vapors and solvents), the application thereof being effected primarily via a printing technique. On the physical basis of the resonance-amplified optical absorption of light (often referred to in the literature as REA for short and protected by the inventor in further patents for the first time in 1995), a printable pigment which serves as a basis for a number of sensory pigment-based inks and labels printed therewith is described here in the structure according to the invention. In detail: Aquareact—nanopigment for reversible detection and quantification of (atmospheric) humidity based on water-reactive polymers; a pigment having a bioreactively changeable nanometrically thin layer for the detection of bacteria and fungi for use in the area of food safety, a pigment having a biodegradable or chemically degradable nanometrically thin layer for the detection of bacteria and fungi for use in the area of food safety, and a novel freezing-thawing indicator pigment for monitoring the cooling chain comprising nano- or microstructures nanometrically degradable (=destructible) by freezing. The invention relates to the particle structure with the use of intelligent gel polymers which are applied to metallic, metal-containing or metal salt-containing pigment carrier particles and in turn are covered with nanoparticles in order to achieve a resonance color effect. The nanoparticles are applied via physical/chemical methods from gas, liquid or from solid suspension. High-vacuum methods (sputtering, high-vacuum vapor deposition, . . . ) are usually not advantageous since they are too expensive for the field of use and are unsuitable for the coating of powders. The resonance color effect structure provides the basis for a novel type of sensory material which generates a signal which can be perceived by the eye and easily optically quantified. The key feature of a resonance color system is a color change caused by an external chemical or a physical stimulation, such as atmospheric humidity, the temperature, ions, pH, microbial activity or molecular interaction.

With the aid of the resonance color technology, a technique which was investigated by scientists of the Universities of Wiener Neustadt (FHWN), Vienna and Graz as well as TUDELFT (NTL), was used for the first time (bio)analytically by Prof. Thomas Schalkhammer and is marketed by Attophotonics Biosciences GmbH, a visual signal is generated by a change in the nanostructure. The principle's of resonance color technology were described in: "Metal nano clusters as transducers for bioaffinity interactions", invited review in Chemical Monthly 129, 1067-1092 (1998) by T. Schalkhammer; "Surface enhanced resonance of metal nanoclusters: A novel tool for Proteomics", Journal of Nanoparticle Research 3, 361-371 (2001) by C. Mayer, R. Palkovits, G. Bauer, T. Schalkhammer. Initial uses of REA nano color technology were published in: "Food-allergen assays on chip based on metal nano-cluster resonance", SPIE 4265, 134-141 (2001) by C. Mayer, R. Verheijen, Th. Schalkhammer, and uses of REA films in Bioanalysis were described in: "Phage display antibody-based proteomic device using resonance-enhanced detection", J. Nanoscience and Nanotechnology 2V3/4, 375-381 (2002) by N. Stich, A. Gandhum, V. Matyushin, J. Raats, Ch. Mayer, Y. Alguel, Th. Schalkhammer.

The use of biodegradable polymers was first developed in a Degree Dissertation of the University of Vienna by K. Hüttner 1999 under the supervision of Prof. Thomas Schalkhammer and further details are described in "Structural behavior of nanometric carbohydrate films transduced by resonant technique", Biopolymers 69 (3), 333-342 (2003) by R. Palkovits, Ch. Mayer, G. Bauer, H. Winkler, F. Pittner, Th. Schalkhammer; and in: "Nanotechnology for smart polymer optical devices", Macromolecular Symposia, 217 (1), 109-134 (2004), H. Rauter, V. Matyushin, Y. Alguel, F. Pittner, T. Schalkhammer; and in "Resonant nano-cluster devices", IEEE Pro. in Nanobiotechnology, 152, 53-63 (2005) by J. Haglmüller, H. Rauter, G. Bauer, F. Pittner, T. Schalkhammer and in "Nanocluster optical resonance devices for molecular structure transduction", Current Nanosciencel, 3-20 (2005) by J. Haglmüller, V. Matyushin, H. Rauter, C. Mayer, H. Winkler, G. Bauer and Th. Schalkhammer; and in: "Nanocluster optical resonance devices for molecular structure transduction", Current Nanosciencel, 3-20 (2005) by J. Haglmüller, V. Matyushin, H. Rauter, C. Mayer, H. Winkler, G. Bauer and Th. Schalkhammer, in particular a detailed description of the use of degradable REA thin layers for use in food sensors being described in the Degree Dissertation by Martin Dragosists, 2005, University of Vienna, supervisor Prof. Schalkhammer, and in detail in the book in the chapter entitled: "Nanocluster Biochips and Cluster Nanotechnology" in "Biochips Nanotechnology" (Copyright December 2005—printed in 2007, American scientific publishers) by J. Haglmüller, M. Dragosists, C. Gauglhofer, M. Koelber-Bauer, Th. Schalkhammer.

Penetration of proteins (enzymes) into the resonance, color-causing layer and the degradation thereof was also described in 1999 by K. Hüttner et al. and stated several times later on (in detail in 2005, also as a means for detecting the bacterial contamination of food).

The following are known from the literature: U.S. Pat. No. 5,611,998, Optochemical sensor and method for production, and the reissue derived therefrom: U.S. RE 37412, Optochemical sensor and method for production, a polymeric spacer layer in an optical thin-layer setup being caused to swell or shrink by the action of a low molecular weight analyte. An irreversible change is likewise described in this patent. The present application can and will therefore not rule out a partial dependence on this patent but is based on this technology in specific applications.

U.S. Pat. No. 6,669,906, Reinforced cluster optical sensors, Schalkhammer et al., is also known, the bond between the reflector layer and a nanoparticle being produced by a specific molecule. The change in this bond leads to an optical signal. The present application can and will not rule out a partial dependence on this patent but is based on this technology in specific applications. Further patents of the inventor of the present application in the area of resonance color technology describe other fields of use, for example "Optical sensor with nanoparticles transfer", WO2005054857—2005 Jun. 16, or other methods for detecting pathogens in foods, e.g. "Automated process for detecting pathogenic organisms in water", US2004241828—2004 Dec. 2.

The intelligent "nanoink" serves for guaranteeing the product quality, optimizing the storability, indicating the status of, for example, food, preserving the nutrient value thereof by correct storage; it indicates the development of odors and the change in aromas, and primarily the occurrence of microbial growth in packed food at the place of its use. The novel nanopigments can be used for a multiplicity of printable indicators which can indicate the state of a product, including: oxygen content, moisture, CO2 concentration, ethylene, integrity of the product, concentration of preservatives, ethanol emitters, status of antibacterial films, antioxidants, flavor absorbers, release systems, lactose values cholesterol, monitoring of the state of microwave-heated products ("cooking state"), status of "microwave packaging systems", freezing and thawing processes and much more. Nanoinks for the following products can be produced with the use of the structure according to the invention: atmospheric humidity in food, electronics and pharmaceuticals, freezing-thawing indication, oxygen leaks in packagings, fish spoilage, meat spoilage, poultry spoilage, rancid butter, milk—indicating the spoilage, yogurt, cream and sour cream, wet cheese—including bacterial infestation, cake, pudding, orange and apple juice and similar juices—spoilage, olive oil, baby food quality control, cooling chain, convenience food, e.g. pizza, microwave-ready, cooking sensor for microwave food, for film-wrapped vegetables, vegetables in jars, cans or preserved food packagings, cut flowers, blister-packed drugs—tightness and spoilage.

Market segments for intelligent and smart products are currently the food industry 45%, beverages 19%, pharmaceuticals 28% and others (cosmetics, toiletry articles, household and electronics) 8% (data, 2002). The integration of intelligent products into the industrial value-added chain is implemented at the level of the raw material supplier 28%, in the case of machinery suppliers 18%, in the case of technology suppliers 22%, in the case of converters 30% and in the case of filling systems 4% and should be transferred to further areas of industry by the intelligent printing ink according to the invention. The moisture-indicating nanoinks according to the invention are generally combined with drying agents and, apart from foods, are marketed with pharmaceuticals, medical equipment, electrical/electronic parts and clothing. The general target market for these printable safety nanoinks is very large; for example the use of plastics films as food wrapping in the USA accounts for more than 50 billion $m^2$ annually. Food packaging applications of drying agents and labels are frequent in Europe and use drop-absorbent nonwovens. The product according to the invention is a printed logo, a surface or a label integrated within a pack, for example of meat and fish, together with moisture regulators on nonwovens. The pigment-based nanoinks described in this patent thus protect consumers from unsafe food if a food packaging material printed with the nanoink indicates to the consumer the presence of spoilage bacteria or fungi and gives an unmistakable visual signal to the consumer, retailer or inspector.

Food deteriorates in its properties as a result of a plurality of independent processes or in combination by physical, biochemical and microbiological changes.

Initial food changes are generally based on chemical changes, oxidation reactions, fat cleavage and both enzymatic activity and microbiological attack with release of toxins. These can change any food and make it unsuitable or unsafe for human consumption. For the use of intelligent packaging material, it is of considerable interest to produce color indicators which are very simple and economical and moreover can be integrated into existing production lines. The nanoink system according to the invention can be applied with commercially available printing equipment. The inks are either preprinted or, if this is not feasible, the products are printed online during the packaging process with up to 50 m/min and 1000 tests per $m^2$. The storability of the nanoinks and of the objects printed therewith must be at least more than one year and must be stable in a wide temperature range.

Typical fields of use of smart nanoinks are a printed surface on packagings for fresh food (meat, sausage, poultry, fish, cheese, vegetables), on milk products (microbial status, odor, taste), for detecting the status of added preservatives, the status of light or UV protection, the water content and status of gas permeability (which is required by the product)—in the case of dry food, in particular chips, snacks, herbs, marinades, coffee, prebaked food—the product should be well protected from atmospheric humidity in order to remain crisp, tender and flavorful.

Moreover, the microbial status as well as oxidation products of chemicals in the area of hygiene products, e.g. cosmetics (determined by high level of cleanliness and safety) and the microbial status for surgical overalls, masks, "coverware" with a high sterilization level in the medical area are expedient fields of use.

The particular features of smart nanoinks can be summarized as follows. The choice of resonant nanoparticles as signal formers for smart pigments is based on their up to 1000 times higher extinction coefficients compared with conjugated chromophores. Nanoparticle-based analysis makes the binding, the dissociation and the degradation of (bio)molecules directly visible to the eye—a similar direct approach without a resonance effect and without nanoparticles requires additional amplification systems, such as, for example, enzymes (see ELISA), radioisotopes (RIA) or fluorescence immunoassays.

The advantages according to the invention of REA pigment nanoinks are based on:
signal visible to the eye
stability—(virtually) no fading (in contrast to chromophores and fluorophores)
all colors with identical chemical
machine-readable—e.g. as printed barcode
extremely little material consumption owing to nanothickness
protection of resources
processable with standard printing systems
printable on site with any desired layout
multi-analyte capabilities through any number of pigment nanoinks The structure of resonant color systems has already been described in prior patents of the applicant, e.g. EP0677738; in short: the structure was based on an optochemical sensor for measuring material concentrations with a reactive sensor layer. These REA optochemical sensors are based on the fact that a chemical reaction between the sensor material and the analyte leads to a change in the optical properties of the sensor. A change of the optical properties may lie, for example, in a change in the absorption or the fluorescence properties, so that the reaction is subsequently detectable by spectroscopic methods.

Sensors of the type mentioned at the outset are substantially characterized in that they have a mirror layer, a reactive, in particular swellable matrix and a layer of a multiplicity of islands of electrically conductive material, in particular metal. In such a sensor, use is made of the property of sensor materials to change the volume reversibly under the influence of the chemical environment present in each case. In addition to this reversible use of the optical sensor, optochemical sensors which cannot be used again after having been used once are of course also of interest. Such optochemical sensors can utilize reactions which lead to the chemical destruction of the metal island structures, it being possible, for example, to dissolve gold islands by in-situ development of hydrogen peroxide by oxidase enzymes and reaction with potassium iodide to give a gold etch solution. Finally, for example, glucose, glutamate, lactate or the like can, by direct reaction of the analyte with the enzyme, lead to a chemical destruction of the structure and can therefore be employed for use as a disposable sensor, cf. EP0677738 and the like.

On this basis, sensors were described which, through destruction of the intermediate layer by enzymes, for example from a food or from food germs, optically indicate the state thereof and was described after preliminary work by K. Hüttner, Degree Dissertation, University of Vienna, supervisor Prof. Schalkhammer, 1999, in the Degree Dissertation of Martin Dragosists, 2005, University of Vienna, supervisor Prof. Schalkhammer, and in detail in a book in the chapter entitled: "Nanocluster Biochips and Cluster Nanotechnology" in "Biochips Nanotechnology" (Copyright December 2005—printed in 2007, American scientific publishers) by J. Haglmüller, M. Dragosists, C. Gauglhofer, M. Koelber-Bauer, Th. Schalkhammer, and the feasibility and applicability thereof was shown by showing the proteolytic digestion by the penetration of proteases into the intermediate layer with digestion thereof by proteinase K, proteinase N, protease from *Aspergillus niger*, Chymotrypsin and collagenase and demonstrating it on real pieces of meat themselves.

Smart sensors for food are often divided into:
1. Time/temperature indicators and integrators and
2. Threshold indicators which provide a visual (irreversible) indication if, for example, a limiting temperature was exceeded (e.g. freezing indicator), and further highly developed indicators of pathogens, described, for example, in Method and apparatus for detection of multiple biological materials with a heterogeneous antibody mixture, U.S. Pat. No. 6,696,264, Feb. 24 (2004), Toxin Alert Inc. (TOX-V and TOXAF-OTC); Biological material detecting articles of manufacture, U.S. Pat. No. 6,867,052 (2005), T. Lander, W. Bodenhamer, or Method and apparatus for detection of multiple biological materials with a heterogeneous antibody mixture, WO 2002/084251 by Toxin Alert Inc., W. Bodenhamer.

The aim of the structure according to the invention is not the development of sensors but a simpler and more economical system based on pigment particles, preferably of a lamellar nature, which are suitable as printing ink or ink for producing colored imprints generally visible to the eye and having sensory properties.

It is very difficult to develop uniform and homogeneous polymer gel films for resonance color pigments, i.e. which are suitable for smart nanoinks and have no artefacts, holes, dirt particles, scratches and in particular an exact homogeneity of the thickness (which is visible as a color effect) since standard methods, such as high-vacuum coating or printing methods are not suitable and cannot be used for applying the color-relevant reactive gel layer (as were described in all preceding patents for the structure of sensors on plastics films, glass or similar surfaces).

Resonance color pigment nanoinks permit a signal indication which is detectable with the naked eye without instruments and in this way are ideally suitable for application to packagings, films or products themselves. Based on this principle of degradable gel layers in resonance color sensors [Degree Dissertation of M. Dragosists 1995], which however are far too expensive for use in the food sector by employing vacuum technology and the like, it was surprisingly possible to develop pigments which were likewise suitable for the detection of food changes. The simple and linear idea of measuring the activity of enzymes from foods with the aid of reactive and biodegradable polymers was achieved by particle suspensions of lamellar pigments which were covered by a plurality of layers.

There is considerable interest here in the use of polymers which exhibit a fundamental structural change on small changes in the environmental parameters. Such behavior characterizes those types of polymers as possible materials for smart nanoinks. Well known stimuli are atmospheric humidity, the temperature, pH and ionic strength. The temperature is the most frequently used stimulation in reactive polymer systems. If such a polymer solution (e.g. poly-N-isopropylacrylamide, PIAA) exhibits a phase below a certain temperature and a phase separation occurs above said temperature, this temperature is referred to as the phase transformation temperature (Tc). These polymers show solubility at one temperature and collapse and precipitation at another, generally higher temperature. The "cloud point" of a polymer relates to that temperature at which the phase separation is observed. Polymers such as PIAA, polyethylene oxide, polymethyl vinyl ether and many others show this effect and can be used for temperature-sensitive nanoinks.

The simplest pigment-based nanoinks arise from the use of water-reactive polymers. Here, the carrier pigments, after sufficient corrosion protection, are coated with water-swellable polymers, for example based on poly-N-vinylpyrrolidone, polyacrylates, polyvinyl acetate copolymers, e.g. of the types 37, 55, 64, 73, modified polyoxazoli(di)nes, e.g. 2-ethyloxazoline, polyamines, e.g. polyallylamine, or the like. After application of corrosion-stable nanoparticles and embedding of the pigment in a carrier matrix whose water-binding behavior does not interfere with that of the reactive gel polymers, a nanoink sensitive to atmospheric humidity forms. Surfaces, characters or printed objects printed with this ink will exhibit a color effect by swelling of the nanopolymer gel layer, depending on the polymer used (e.g. polyacrylates from as low as 10% relative humidity and PVP-polyvinyl acetate copolymers having a higher proportion of PVAc only close to the dew point). For crosslinking of the polymer layer, the reactive polymer on the pigment can be exposed to the light of a UV-Hg vapor burner or of a medium-pressure lamp, which bring about gel network formation—in this way, the stability can be increased and the degree of swelling adjusted.

For testing and for calibrating the moisture-reactive nanoinks, saturated aqueous solutions of various salts having a high proportion of undissolved precipitate are in use and, under given conditions, are packed together with the product for calibration.

The use of pigment binders without separate strong binding of water but with a pore-like character gives products having advantageous properties (e.g. porous polypropylene). Sensory moisture-indicating pigments can be used in many areas, for example foods, packagings, pharmacy, paper and electronic products.

The pigment-based nanoinks with suitable gel polymers as intermediate layers are sensitive to bacterial enzymes and showed a direct correlation with the bacterial growth. The challenge for this invention was to coat the carrier particles consisting of metal (or metal-containing or consisting at least of water-insoluble metal salts) with an extremely homogeneous layer thickness with stable (bio)polymeric layers having a layer thickness of up to 1 micron in an industrially viable method. In order to achieve a stable coating, it was often necessary first to coat the pigment carriers, for example comprising aluminum, with an adhesive or corrosion protection layer of one nanometer to about 1 µm (preferably 1-300 nm, particularly preferably 3-150 nm). However, it is also necessary to stabilize the spacer layer comprising polymers, often by additional methods, but crosslinking by hard crosslinking agents (isocyanates and the like) should be avoided for toxicological and chemical reasons since they retard or completely prevent the degradation by the enzymes (e.g. proteases, lipases, glycosidases or DNAases) or give toxicologically unsafe degradation products.

Protein films or analogous polymer films are available in great variety and serve as smart layers (reference numeral 3), i.e. as "transducers". However, it is important to keep the protein in its 3-dimensional structure accessible to attack by enzymes. "Protein gels" are applied to the carrier pigments by adsorption, crosslinking, precipitation or polymerization methods to the particles from liquid phase=solution. The concentration of the protein solution in these methods is often relatively high (e.g. 5% strength) so that there is a significant cost factor and availability of the protein in sufficient amount is essential.

Pigment-based nanoinks are, however, also directly sensitive to bacterial proteins without enzymatic activity and the color of the pigments shows a direct correlation with proteins, for example from a food or from bacterial growth. Release of nanoparticles bound to the pigments can also take place with cleavage of biorecognitive bonds primarily based on the displacement of a reversible antibody-antigen interaction. A layer of (bio)recognitively bound nanoparticles is the basis of an REA color on the pigment particles due to resonance between the pigment surface and this layer of bound particles.

The fact that the particles exhibit a color effect on site and this is changed by the analyte avoids a limiting factor of the analysis in solutions, namely the diffusion of reagents. For these nanoparticle "release" pigments, the choice of the surface chemistry which is used for binding chromophoric nanoparticles to the surface thereof is decisive since, after contact with the analyte from their (bio)recognitive interaction, they must be released from this surface. On the other hand, release of nanoparticles must not take place too easily, in order to prevent an unspecific reaction. On the basis of data (Schalkhammer and Gauglhofer—Degree Dissertation 2005, University of Vienna), nanoparticles tend to undergo unspecific adsorption in particular through high surface charge and the high density of adsorptive binding sites. Extreme care is therefore needed in order to bind particles in a manner permitting release again. Every drying of the nanoink leads to the accumulation of particle aggregates and often to a completely irreversible separation. Only suitably generally water-containing gel base materials are capable of providing the necessary local water environment for reversible protein particle chemistry. Moreover, the binding partners must be correctly designed to permit efficient but reversible crosslinking. The use of such nanoparticle "release" pigments is not restricted to protein quantification for the food status but can also be used for DNA analysis, medicine and diagnosis. However, it must be emphasized that all reversible processes of high affinity (e.g. antigen-antibody) require at least a few hours but often days for equilibrium to be established—ideally for slowly responding intelligent pigments—but not for the "normal" analysis in the laboratory.

Freezing-thawing indicator pigments for nanoinks based on the structure according to the invention and are also obtainable in a simple manner capable of providing an optically detectable indication as to whether a frozen article, such as a frozen food, has been thawed briefly (or for longer) after this time.

Conventional indicator labels, for freezing-thawing processes, make use of, for example, meltable liquids in order to produce a visible color change after the undesired thawing and generally have dissolvable or breakable separating walls or partitions which break when the label has been completely frozen. On later melting, one the liquids emerges here in order to mix with a further reagent and thus to give a visible color change.

Such types require the use of partition materials, macroscopic films or labels. The nano-REA pigments according to the invention have a reactive intermediate phase between the carrier particle surface and the nanoparticles, which reacts with chemicals released from small capsules, with a change of color. On freezing, the micro- or nanocapsules in the carrier matrix according to the invention become fissured and, within the next thawing phase, the reagent released (e.g. enzyme, acid, base, strong binding agent) irreversibly attacks the intermediate layer—which leads to a visible color change. A biodegradable polymer—a polyester—as reactive gel and, in the capsules, an esterase can be used as a simple example. Poly-N-vinylpyrrolidone (PVP) as a gel and, in the capsules, a tanning agent can be used as a nonbiochemical example—tanning agents lead to virtually irreversible crosslinking of PVP gels and hence to a color change.

In particular the combination of sensory pigment-based nanoinks with their ability to inscribe through heat, light and chemical inkjet printing (chemically reactive inkjet inks) proves to be particularly advantageous.

Pigment-based nanoinks for monitoring organic solvents and organic chemical vapors are permitted through the use of hydrophobic polymer networks. A hydrophobic polymer, such as, for example, polypropylene, polybutadiene or related polymers, enable the concentration of volatile organic solvents in the gas phase to be converted into a reversible optical signal. If a color effect is not sufficient for identification, a plurality of different nanoinks can also form a color array and the detection of the components can be derived from pattern recognition, for example for odors or for discriminating between gasoline and diesel.

Today, colored pigments are part of the prior art and are used in a multiplicity of products of daily life. A multiplicity of pigments can serve as carrier material for the structure according to the invention, for example those of Merck KGaA (based on metal oxides), from Schlenk (based on metals) and many other manufacturers. Known trade names are Iriodin®, Biflair® or Xirallic®. Silica (SiO2), titanium dioxide (TiO2), mica or glass can also be used as carrier materials for pigments. The diameters of typical carriers are from 1 to 300 μm, depending on the field of use. One or more layers of different metal oxides having a thickness of up to several hundred nm are applied to these flakes by in general chemical deposition techniques. The difference between the refractive indices (e.g.: ND [SiO2]=1.46; ND [TiO2]=2.4) of these layers generates different basic colors (which are changed according to the invention by the REA effect).

According to the invention, it was surprising to find that pigments comprising metal oxides or metals (all metals or semiconductors having a reflective surface, e.g. Al, Au, Ag, Cu, brass, Ti, Ni, Co, (stainless) steel, Pd, Pt, Sn and alloys thereof), when coated with the nanolayers described further above, give novel intelligent inks. There are to date no pigments or inks having resonant color effects which change their color in an intelligent manner reversibly or irreversibly as a result of an external stimulation via chemical components (from atmospheric humidity to food status).

The reactive polymer (3) is bonded by ionic, hydrophobic or covalent bonds to carrier particles or it is directly "polymerized onto" the particle surface (e.g. chain extension of acrylates on an anchor molecule having a silane function which can bind directly to metal oxide surfaces).

Living/controlled free radical polymerization, abbreviated to LFRP or CFRP, is a polymerization process in which the advantages of free radical polymerization are linked to the advantages of a living polymerization by a targeted choice of the reaction conditions.

This permits polymerizations and copolymerizations which are not very sensitive to dirt, in which a large selection of monomers can be used, which take place under relatively mild reaction conditions, which give very uniform polymers having a narrow molar mass distribution and which permit controllable polymer architectures. The most important processes are inter alia: atom transfer radical polymerization (ATRP), initiator: organohalide RX, free radical buffer: transition metal complex compound MXnLx; stable free radical polymerization (SFRP), free radical buffer: stable free radicals based on linear or cyclic nitroxides, e.g. (chemistry); reversible addition fragmentation chain transfer polymerization (RAFT), initiator: peroxo or azo compound, more rarely also photoinitiators or gamma radiation, controlling species: substituted dithioesters, xanthates or trithiocarbonates. In the controlled RAFT polymerization, ideally the polymerization rate is unchanged compared with the conventional free radical polymerization. Depending on the structure of the RAFT agent used, however, there may be negative deviations, which are designated as so-called "retardation" of the rate.

For building up the layers, atom transfer radical polymerization (abbreviated to ATRP below) is an important method for the production of a multiplicity of polymer layers, such as, for example, polyacrylates, polymethacrylates and polystyrenes. The ATRP method was developed in the nineties, principally by Matyjaszewski et al. The ATRP produces (homo- or hetero-) polymers having a narrow distribution in the molar mass range up to about 120 000 g/mol. A particular advantage is that both the molecular weight and the molecular weight distribution therewith the layer thickness (the layer with the reference numeral 3) can be regulated. As a living polymerization, it furthermore permits targeted buildup of polymer architectures with different monomers as block copolymer layer structures.

Since free radicals are very reactive, the termination of active chains by recombination or disproportionation can be prevented only by keeping the concentration of the active centers very small (typically: $c=10^{-9}$ mol/l, cf. with "normal" free radical polymerization: $c=10^{-6}$ mol/l). For this purpose, a system which forms so-called "sleeping radicals" with the growing polymer chains is added to the reaction. The radicals react reversibly to give a non-radical species. The polymerization-active state is restored by dissociation of these sleeping radicals. Such a system is Cu(I) LnBr/Cu(II) LnBr2 (where Ln=e.g. 2,2'-bipyridine):

The above equilibrium lies on the side of the sleeping radical R—X. Consequently, the concentration of free radicals is very low. However, before a free radical is deactivated again by the copper complex, it can pass through some growth steps, the number of growth steps per free radical being the same on average. This results in the formation of a virtually monodisperse polymer. Ideally, the following assumptions are made with I with ki to R* and R*+M with Kt to R–M*: a) ki>>kp ⇒ all initiator molecules have already started before the growth reaction begins. b) ktr, kt≈0 ⇒ transfer and termination reactions can be neglected. c) kp is of the same magnitude for different chain lengths.

Nanoparticles (reference numeral 4) comprising corrosion-stable metals or semiconductors (cf. also carrier particles), e.g. Au, Ag, Cu, Pt, Pd, ... are applied from solution by adsorption or chemical bonding or deposited by in-situ reduction (corresponding to the literature, e.g. silver with dimethylformamide or by means of polyol chemistry) directly on the surface of the polymer from precursors.

Colored nanoparticles (reference numeral 4) are obtainable by a multiplicity of methods and are bound from solution or gas phase or adsorbed as powders. Anionic dyes are deposited directly from aqueous medium on pigments which have, for example, amino groups. Mordant dyes are bound in insoluble form as particles with complex formation with chromium (III), iron(III) or aluminum salts. Disperse dyes (water-insoluble dyes) are quasi-(nano)particles which, owing to small particle size and additional wetting agents, are not dissolved in water but are readily dispersible and also color surfaces which have no free-NH2 or —OH groups. Ingrain or coupling dyes are applied to the pigments in two steps. Cationic dyes are preferable on anionically modified pigments. Vat dyes are water-insoluble dyes which are brought into their soluble leuco form by reduction and are precipitated onto the carrier pigments as colored colloid (e.g. indigo, purple, indanthrenes, for example Blue RS and C.I. Vat Yellow, C.I. Vat Orange, C.I. Vat Red, C.I. Vat Violet, C.I. Vat Blue, C.I. Vat Green, C.I. Vat Brown and C.I. Vat Black. Metal complex dyes and reactive dyes with particulate deposition are also suitable as nanoparticles. Particularly suitable are pigment dyes which acquire pigment properties by laking, if need be, a basic function on a sulfone, phosphate or carboxyl group. Acid Blue 3, Acid Blue 7, Acid Blue 9, Acid Green 81, Acid Red 33, Acid Red 274, Acid Yellow 23, Sunset Yellow, Basic Violet 10, Disperse Blue, Disperse Orange, Disperse Back and/or reactive green are mentioned here by way of example.

Important pigments for nanoparticles (reference numeral 4) are monoazo pigments: Pigment Brown, Orange, Red and Yellow, disazo pigments: C.I. Pigment Orange, Red and Yellow, anthanthrone pigments: C.I. Pigment Red, anthraquinone pigments: C.I. Pigment Yellow and Violet, anthrapyrimidine pigments: C.I. Pigment Yellow; quinacridone pigments: C.I. Pigment Red and Violet, quinophthalone pigments: C.I. Pigment Yellow, dioxazine pigments: C.I. Pigment Violet, diketopyrrolopyrrole pigments: C.I. Pigment Orange and Red, flavanthrone pigments: C.I. Pigment Yellow, indanthrone pigments: C.I. Pigment Blue, isoindoline pigments: C.I. Pigment Orange, Red and Yellow, isoindoline pigments: C.I. Pigment Orange, Red and Yellow, isoviolanthrone pigments: C.I. Pigment Violet, metal complex pigments: C.I. Pigment Yellow and Green, perinone pigments: C.I. Pigment Orange and Red, perylene pigments: C.I. Pigment Black, Red and Violet; phthalocyanine pigments: C.I. Pigment Blue and Green, pyranthrone pigments: C.I. Pigment Orange and Red, thioindigo pigments: C.I. Pigment Red and Violet, and triarylcarbonium pigments: C.I. Pigment Blue, Green, Red, Black, Yellow and Brown. Dyes which are oil-soluble (=sufficient solubility in organic solvents) and can be precipitated by solvent change (addition of nonsolvent), such as Disperse Blue 3 (C.I. 61505), Disperse Blue 14 (C.I. 615006), Disperse Orange 1 (C.I. 11080), Disperse Orange 3 (C.I. 11005), Disperse Orange 11 (C.I. 60700), Disperse Orange 13 (C.I. 26080), Disperse Red 1 (C.I. 11110), Disperse Red 13 (C.I. 11115), Disperse Yellow 3 (C.I. 11855), Disperse Yellow 7 (C.I. 26090), Disperse Yellow 9 (C.I. 10375), Sudan 1 Yellow (C.I. 12055), Sudan II Orange (C.I. 12140), Sudan III Red (C.I. 26100), Sudan IV Red (C.I. 26105), Sudan Black B (C.I. 26150), Sudan Blue 1 (C.I. 61552), Sudan Blue 11 (C.I. 61554), Sudan Orange G (C.I. 11920), Sudan Red 7B (C.I. 26050), Solvent Violet 13, Solvent Blue 59, Solvent Green 3 or Solvent Red, can also advantageously be used for producing the nanoparticles (reference numeral 4).

Suitable inorganic nanoparticles (reference numeral 4) are, inter alia, iron oxides (C.I. No. 77491, 77492, 77499), Ultramarine (C.I. No. 77007), Prussian Blue/Ferric Blue (C.I. No. 77510), carbon black (C.I. No. 77267), chromium oxide green (C.I. No. 77288), chromium oxide hydrate green (C.I. No. 77289), manganese violet (C.I. No. 77742), metal sulfides, metal oxides and suboxides and metals, such as copper (C.I. No. 77400), bronze (C.I. No. 77400), brass (C.I. No. 77400), silver (C.I. No. 77820) or gold (C.I. No. 77480).

The nanopigments (composed at least of: pigment particle (1), reactive polymer nanofilm (3) and nanoparticle layer (4)) must be formulated with a generally liquid carrier matrix (generally polymer solution, adhesive emulsion or particle suspension) in order then to be applied in general as a film of about 40-400% surface coating to a surface. In this way, it is also possible to print, spray or spread semitransparent layers so that the goods are still visible. Solvents, viscosity and "adhesion chemistry" for the nanoinks must be optimized for the printing, spraying or spreading, depending on application and material.

These sensory pigments are used in foods, packagings, pharmaceutical products, paper and electronic products as liquid ink or printing ink for printable indicators which can indicate the state of a product, in particular the oxygen content, moisture, CO2 concentration, integrity of the product, status of antibacterial films, antioxidants, lactose content, cholesterol content, monitoring of the state of microwave-heated products ("cooking state"), status of "microwave packaging systems", freezing and thawing processes, state of vaccines, leaks in food and blister packs, on test areas and test strips for fish spoilage, meat spoilage, poultry spoilage, rancid butter, milk spoilage, spoilage of yogurt, cream and sour cream and cheese, cake, pudding, fruit juices, olive oil and baby food, compliance with the cooling chain, status of convenience food, e.g. pizza, microwave-ready, cooking sensor for microwave food, state of film-wrapped vegetable and of vegetable in jars and cans or preserved food packs and the freshness of cut flowers.

The application of the sensory pigments for use in foods, packagings, pharmaceutical products, paper and electronic products as liquid ink or printing ink for printable indicators is effected in a manner such that in general at least 25 pigment particles are printed in order to print a visible field of more than 25 mm$^2$.

The application of sensory pigments for use in foods, packagings, pharmaceutical products, paper and electronic products is effected as liquid ink or printing ink for printable indicators in flexographic, gravure and offset printing presses and spray and stamp systems.

The application of the sensory pigments for use in foods, packagings, pharmaceutical products, paper and electronic products as liquid ink or printing inks is suitable for printable indicators as a barcode or together with barcode and laser inscription.

A typical structure and sequence is:

layer 1: metal nanoparticle 1-50 µm wide and 0.1 to 5 µm thick layer 2: corrosion protection layer on the metal nanoparticle 1-100 nm, comprising, for example, oxides ($Al_2O_3$, $SiO_2$, phosphates, . . . ) or polymers, inert, non-swelling layer 3: 50-300 nm thick, water-swelling layer of a (bio) polymer layer 4: metal or semiconductor nanoparticle, sub- to a few monolayers thick (depending on size and extinction coefficient)

Pigment suspended in material 5: formulation comprising lake for formation of a generally porous layer, e.g. comprising tacky microspheres and the like, solvent must be compatible with the (bio)polymer of layer 3.

On the user's premises: printing of the nanoink on different materials by standard processes The invention is illustrated in examples of use:

EXAMPLE 1

Color Effect on Material Having a Relatively High Refractive Index

A layer of aluminum oxide, zirconium oxide, tin oxide, titanium oxide, niobium oxide, iron oxide or related materials, such as nitrides or oxynitrides, is applied to pigments (1) comprising ceramic (e.g. mica), glass or metal by chemically reactive deposition in solution and gas phase. These oxides have efficient reflection of light at the phase boundary.

Alternatively, pigments, for example from Merck, which already have the abovementioned layer sequence can be used. Known trade names are Iriodin®, Biflair® or Xirallic®.

Thereafter, a layer of organic intelligent polymers having a low refractive index is applied with a thickness of from 5 to 500 nm (preferably 5 to 200 nm) from solution.

Then, metallic, semiconductor (e.g. Ge, Si, C) or chromophoric (=dye) nanoparticles are bound to the surface of the polymer by adsorption from a suspension thereof.

The pigment formed is suspended in a solvent and printed onto a surface. Here, either an adhesive polymer can be added to the solution to bind the pigments or the surface itself can first be rendered tacky and the pigments then applied thereon (e.g. pressure-sensitive adhesive, peelable film with adhesive layer underneath, adhesive particle coating . . . ).

EXAMPLE 2

Color Effect with Semitransparent Structure

A non-impermeable particle layer of a metal or of semiconductor nanoparticle (e.g. Ge, Si, C, metal sulfides, metal oxides, metal suboxides) of suitable adhesion and corrosion stability is first applied by chemical methods to the pigment surfaces (1) or the surface of a layer having a high refractive index (cf. example 1).

Suitable metals here are, for example, gold (generally only with adhesion layer, stable but expensive), silver (moderately stable and poorly adhering), palladium, titanium, niobium, chromium, nickel, tin, carbon black or the like.

Colored nanoparticles of thermally stable dyes can be applied directly by vapor deposition in a "sublimation-fluid-

EXAMPLE 3

Adhesion Promoter and Adsorption of Nanoparticles

Lamellar or fibrous particles comprising ceramic (e.g. mica, kaolin, talc), glass or metal preferably serve as pigments (1). In order to achieve optimum adhesion, the material is generally first coated with adhesion-promoting silanes. The silane is generally sprayed onto the oxide layer and baked (generally from 80° C. to 160° C.). The silane layers are crosslinked during this procedure. In general, methoxy-, ethoxy- or chlorosilanes having suitable functional groups for binding the polymer, e.g. vinyltriethoxysilane, various epoxy, e.g. glycidylsilanes, aminosilanes, e.g. aminopropyltriethoxysilanes, mercaptopropyltrimethoxysilane and the like, serve as the silane.

Thereafter, the reactive polymers are bound to the surface by precipitation of said polymers from solution, whereby strong adsorption or covalent chemical bonding should advantageously take place on the particle surface.

Nanoparticles can also be applied as colloids from a concentrated (>>100 mg solid/1) solution and chemically or adsorptively bound. Colloidal solutions of relatively low concentration are generally unsuitable (owing to the long process time) for industrial processes. Chemically labile colloids comprising, for example silver or copper are generally protected with glass, ceramic or polymers before use and are coated with a 1-100 nm thick layer thereof before being employed. Particle-protecting polymers may be charged so that they bind with high affinity to the oppositely charged surface of the thin layer and thus facilitate the adsorption thereof. Hydrophobic attractive forces, too, can advantageously be used here.

EXAMPLE 4

Embedding Material

Reactive pigments prepared according to examples 1 to 3 are coated with a spray-coating, knife-coating or dip-coating lacquer comprising, for example starch solution, polyacrylates, polymethacrylates, poly-urethanes or epoxy resin and the intelligent nanoinks are thus produced.

In order to enable separation of nanoparticles from the gel matrix, the lacquer must not bond irreversibly to the nanoparticles. Here, either a deliberately unstable component can first be applied over the particles before they are embedded in the lacquer (for example thin layer comprising water-soluble polymer), the polymer itself may be biodegradable or chemically degradable (e.g. protein layer) or a porous matrix with which the pigment particles are surrounded but not directly covered (e.g. latex suspension of tacky latex particles (generally a few μm in size) which fix the pigments to the object but do not coalesce to form a cohesive film (e.g. particle latex comprising polystyrene or PVAc, thermally bonding) can be used. After printing, the lacquer is dried and if necessary hardened at elevated temperature. With the use of commercial lacquer systems, the exact hardening conditions are to be chosen according to the lacquer manufacturer's information. An object may also be coated with polymer solution by spray, spin or dip coating processes, the solvent then removed and the film crosslinked by UV radiation (e.g. acrylates), electron beams or thermally.

EXAMPLE 5

Sol/Gel Process

Analogously, intelligent pigments are also coated with sol/gel lacquers. Typical raw materials here are metallates of titanium (e.g. titanium ethoxylates), tetraethoxysilane, zirconium metallates or similar compounds which generally react with water with hydrolysis first to give hydroxides and, after thermal treatment, to give crosslinked, chemically-mechanically stable oxides having good surface adhesion. A multiplicity of commercially available products can be used here. The layer thickness of the nanoparticulate layers generally deposited here is from about 10 nm to a few microns, depending on the application.

According to the invention, a layer of SiO2 nanoparticles can be deposited by alkaline hydrolysis (e.g. with ammonia) of tetraethoxysilane over water-reactive pigments based on poly-N-vinylpyrrolidones, without destroying the reactivity of the pigments.

EXAMPLE 6

Reactive Polymers for Water-Sensitive Nanoinks

Primarily, hydrogels (poly-N-vinylpyrrolidones, if need be crosslinked by UV, electron beams or bisazides), ionic polymers (polyacrylic acid (co)polymers, . . . ), polymethacrylates, polysulfonic acids and the like, generally in combination with more hydrophobic molecules, e.g. polyvinyl acetate, but also various polyamines, can successfully be used here. The exact reaction conditions are highly material-dependent and depend on the water-binding capacity of the polymers.

EXAMPLE 7

Deposition of Semiconductor Nanoparticles 50 g of metallic pigment having an adequate corrosion protection layer, coated mica, coated glass lamellae or finished colored commercially available pigment lamellae having a particle size of about 1-200 μm are coated with a polymer of choice by adsorption thereof and precipitation of the required layer thickness. Thereafter, 0.5-4 g of carbon black (mean particle size: 10-40 nm, or other nanoparticles) are admixed and stirred. After the deposition of the particles, the particles are filtered off, washed with water and dried.

EXAMPLE 8

Binding of the Nanoparticles (4)

Pigments (1) having a reactive polymer layer (3) (for establishing the desired sensitivity and the shade) are coated with a soluble metal salt or a suspension of very fine particles, preferably having a size of less than 100 nm, from the group consisting of the metals V, Cr, Mn, Fe, Co, Ni, Cu, Ag, Sn, Pb, C, Si, Ge and Bi. The process can be promoted by precipitation by means of a pH change, solvent change or addition of an anion having precipitating properties.

These particles are either themselves chromophoric or formed from a precursor by reduction in-situ (with, for example, hydrazine, sodium hypophosphite, ascorbic acid, polyols, . . . ).

In order to permit a strong color, the mean material thickness should be about 5 nm in the case of metallic particles and, proportionally to their extinction coefficient, more in the case of chromophoric particles.

EXAMPLE 9

Covering Layer

Particles according to one of examples 1-8, preferably mixed with a polymer, are applied to the surface of an object. Thereafter, a further covering layer comprising a preferably organic polymer is applied. The layer thickness of the covering coat is from 0.1 to 100 µm, preferably from 1 to 20 µm. The covering layer serves not only for protecting the print layer but can also contain chemically important components and in particular suppress the emergence of nanoparticles from the layer.

EXAMPLE 10

Colored Carrier Pigments

In order to achieve a targeted color effect even after the destruction of the REA layer, for example by targeted degradation of a biopolymer (3) (the material would otherwise become silver or whitish), colored pigments can be used instead of white or silver pigments (1). Inter alia, Iriodin® 100, Silver Pearl, 10-60 µm; Iriodin® 103, Rutile Sterling Silver, 10-60 µm; Iriodin® 111, Rutile Fine Satin, 1-15 µm; Iriodin® 119, Polar White, 5-25 µm; Iriodin® 120, Lustre Satin, 5-25 µm; Iriodin® 123, Bright Lustre Satin, 5-25 µm; Iriodin® 153, Flash Pearl, 20-100 µm are known. The colored luster effect pigments, the interference pigments of the 200 and the 7200 series, changes with the direction of observation, the color changes or iridesces. In combination with colored colorants, effects with a strong color change are achievable. Inter alia, Iriodin® 211, Rutile Fine Red, 5-25 µm; Iriodin® 221 Rutile Fine Blue, 5-25 µm; Iriodin® 223, Rutile Fine Lilac, 5-25 µm, or Iriodin® 231, Rutile Fine Green, 5-25 µm are known. Iriodin® Flash interference pigments and Iriodin® Ultra interference pigments are also similar. With the iron oxide-containing Iriodin® effect pigments of the 300 and the 500 series, the gold and metal luster pigments, gold, bronze, copper and red luster effects can be realized.

All pigments can serve as a base carrier for the novel intelligent nanoinks if they have a sufficient size (>>300 nm) and sufficient evenness of the surface (generally lamellar) and hence permit intelligent nanoinks having virtually any desired color change. In particular, intense warning colors (red, orange, yellow) as a base shade permit, according to the invention, the warning of consumers about changed products.

EXAMPLE 11

Carbon Black as Nanoparticle

The oldest route for the preparation of pigments consists in the application of carbon from aqueous suspension with the use of suitable surface-active auxiliaries or by pyrolysis of organic compounds, the carbon of course being deposited on the pigment surface. First, the pigment is mixed with a carbon black dispersion. By addition of a metal salt solution under precipitation conditions, a carbon-containing insoluble metal salt layer is precipitated onto the substrate.

Often, these pigments have a brown-gray character and only matt luster, caused by coarse-particled precipitated carbon agglomerates. Owing to the different substrates, the proportion by weight of carbon may vary.

EXAMPLE 12

Precipitation of Polymers (3) as a Reactive Layer

An alkaline solution of e.g. 4 g of sodium salt of a fairly hydrophobic polymer (e.g. copolymers of polyacrylic acid, polymethacrylic acid, polymaleic acid, polyvinylsulfonic acid, polystyrenesulfonic acid with hydrophobic polymers) or simple compounds, such as stearates or palmitates, or another water-soluble salt of an organic acid in 100 ml of water is metered at a pH of 5-7 into a suspension of 100 g of pigments (see above) having a particle size of 1-60 µm in 1000 ml of water, so that, while keeping the pH constant with acid, the desired substance, e.g. the polymer, is slowly precipitated. Thereafter, filtration and drying are effected. A matt to lustrous powder is obtained.

EXAMPLE 13

Silver as a Nanolayer

Silver can be precipitated onto intelligent pigments. The coating is effected, for example, by reduction of silver salts (analogously also with other metal salts) in the presence of particles in aqueous solution. Metallic nanoparticle layers are known as coatings, for example on quartz, mica, tin oxide or titanium oxide, but also directly on the intelligent polymer layers (3). Silver can be reduced and precipitated, for example, by reduction with sugar (generally 50-100° C.), ascorbic acid, sodium borohydride, hydrazine, alcohols at relatively high temperature (generally 100-200° C.) Often, the surface must be coated with an adhesion promoter, for example a few monolayers of tin silicate or organosilicon compounds.

EXAMPLE 14

Layer Application by Phase Separation

The application of thin polymeric layers can be effected by a phase separation process. Here, a polymer is dissolved in a good solvent and the carrier particles (see above) are added. A poor solvent or "nonsolvent" is preferably added slowly with agitation. The polymer being precipitated is bound as a thin layer, which slowly becomes thicker, to the carrier matrix. All solvents known for the polymer, preferably having low toxicity, favorable price and suitable recycling technologies, can serve as a good solvent, amongst them alcohols, such as, for example, ethanol, methanol, ethylhexanol, ethers, such as tetrahydrofuran, ketones, such as MEK or acetone, solvents from the coating industry, such as, for example butyl(ene) glycols. Often, water is preferred as a poor solvent. All known polymers may serve as polymers—here too, toxicologically safe materials from the coating industry or known plastics are often to be used as a mixture with an adhesion promoter. In the case of proteins (gelatin, BSA, . . . ), precipitation is effected from a solution in water by addition of organic solvent.

EXAMPLE 15

Layer Application by Polymerization

The application of thin polymeric layers can be effected by an in-situ polymerization process. Here, a polymer precursor is dissolved in a solvent which is not too good and the carrier particles are added. Polymerization free radical initiators or polycondensation initiators are admixed with agitation or the temperature is increased. The polymer which becomes insoluble through chain extension is bound as a thin layer, which slowly becomes thicker, to the carrier matrix. All known polymers can serve as polymers, preferably acrylates and methacrylates—here too, toxicologically safe materials from the coating industry or known plastics are often preferably to be used as a mixture with an adhesion promoter (e.g. silanes).

EXAMPLE 16

Layer Application by ATRP In Situ Polymerization

For example, 0.5 mol of CuBr and 0.5 mol of Cu powder are weighed in. 50 mol of monomer (highly charged monomers require specific reaction conditions!), if need be solvent (virtually any desired one—including water) and 1.5 mol of ligand (2,2'-bipyridine, pentamethyldiethylenetriamine, . . . ) are added thereto. The flask is closed and the solution is stirred until a violet color occurs. Thereafter, 0.5 mol of a preferably tertiary bromine compound (other halogens are possible—but reactivity varies very greatly) is added as an initiator (bound as a layer on the surface of the carrier particles). Polymerization is effected for about 4 hours (if need be heated up to about 80° C.) The particles are separated off and the solution is treated with basic aluminum oxide for detoxification.

EXAMPLE 17

Preparation of Organic Nanoparticles by Precipitation

Organic nanoparticles are preferably formed by dissolution in an organic solvent (e.g. N-methyl-pyrrolidone, ethanol and the like) and precipitation in a nonsolvent (e.g. water, benzine and the like). Examples of dyes are monoazo yellow, monoazo orange, disazo, β-naphthol, naphthol-AS, benzimidazolone, disazo, metal complex, isoindolinone or isoindoline pigments or phthalocyanine, quinacridone, perylene, perinone, thioindigo, anthraquinone, anthrapyrimidine, flavanthrone, pyranthrone, anthanthrone, dioxazine, triarylcarbonium, quinophthalone or diketopyrrolo-pyrrole pigments.

EXAMPLE 18

Preparation of Organic Nanoparticles by Sublimation or Vaporization

Organic nanoparticles of thermally stable dyes are preferably formed by sublimation. Examples of dyes phthalocyanine, quinacridone, perylene, perinone, thio-indigo, anthraquinone, anthrapyrimidine, flavanthrone, pyranthrone, anthanthrone, dioxazine, triarylcarbonium, quinophthalone or diketopyrrolopyrrole pigments. The dye is brought into the gas phase and condensed from this by cooling. The cooling can be effected typically by the admixing of cold gas, by spraying in of/passing into liquid or on a cool surface.

Figure 2:
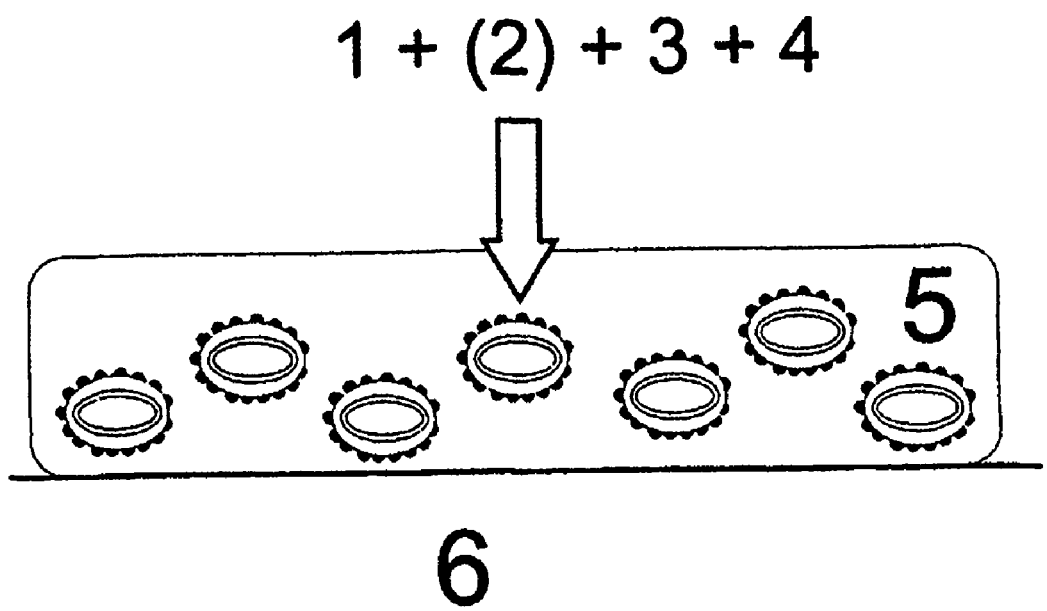

Below, a short description of the reference numerals in the figures and illustrative explanations:

FIG. 1 shows a schematic diagram of the pigment structure. The assignment of the reference numerals is to be carried out as follows:
 1. Particle
 2. Optional intermediate layer<500 nm
 3. Chemically reactive polymer
 4. Nanometric chromophoric particles (1-100 nm)
 5. Embedding material FIG. 2 shows a schematic diagram of the pigment in the "lacquer"=binder (5). The assignment of the reference numerals is to be carried out as follows:
 1. Particle
 2. Optional intermediate layer<500 nm
 3. Chemically reactive polymer
 4. Nanometric chromophoric particles (1-100 nm)
 5. Embedding material=binder
 6. Product (packaging, goods, film, . . . )

Inter alia, swelling gel polymers, hotmelt and pressure-sensitive adhesives (preferably particulate—in order to have as little influence as possible on the chemical behavior of the pigments), adhesive coating on the product itself (the pigments are bound=adhesively bonded only on one side) or a surrounding macroscopic (polymer) film (for enclosing the pigments in a film pocket as "binder") can serve as a binder, it possibly being necessary for the film to be porous or permeable in order to allow the analytes to pass through the pigments.

Figure 3:
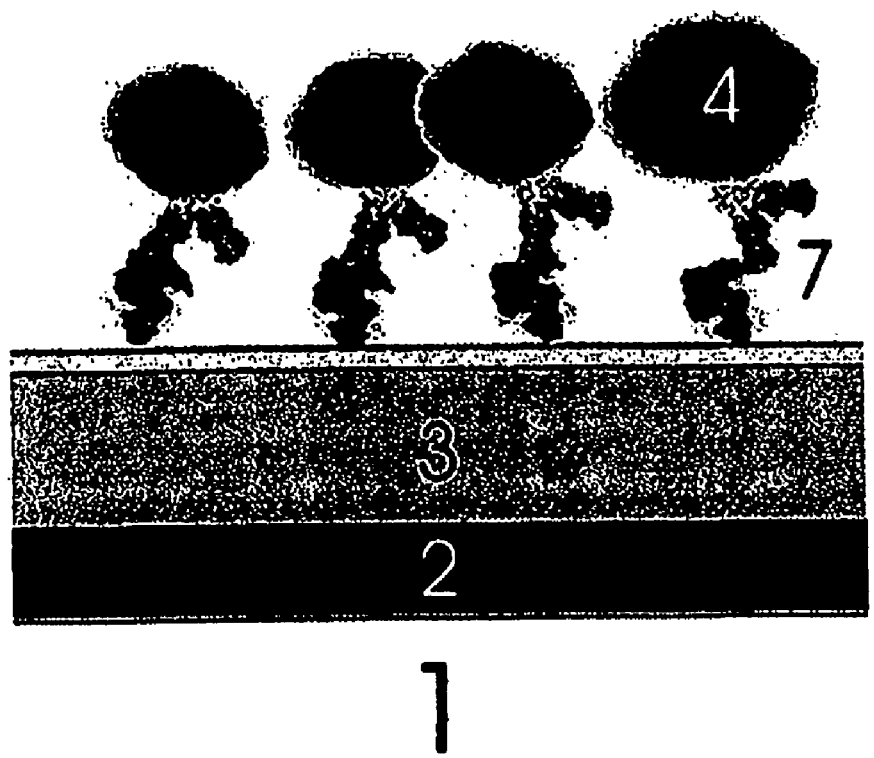

FIG. 3 shows a schematic diagram of a nanoparticle "release" pigment. The assignment of the reference numerals is to be carried out as follows:
 1. Particle
 2. Optional intermediate layer<500 nm
 3. Chemically reactive polymer
 4. Nanometric chromophoric particles (1-100 nm)
 5. Embedding material
 6. Product (packaging, goods, film, . . . )
 7. Reversible binding system displaceable by the analyte molecule A surrounding binder, preferably a macroscopic (polymer) film (for enclosing the pigments but also nanoparticles, for example in a film pocket) generally serves here for retaining any released nanoparticles.

Figure 4:
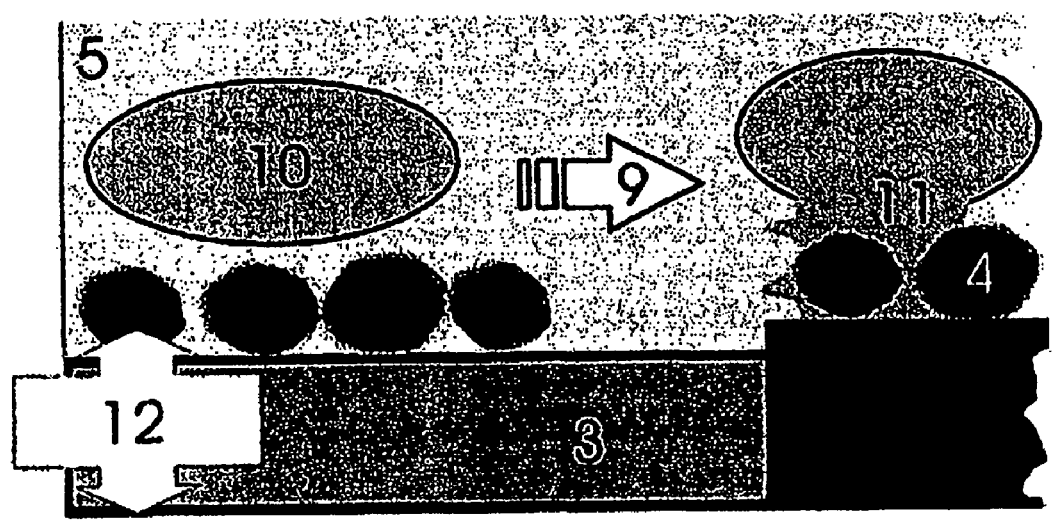

FIG. 4 shows a schematic diagram of a freezing-thawing pigment. The assignment of the reference numerals is to be carried out as follows:
 1. Particle
 2. Optional intermediate layer<500 nm
 3. Chemically reactive polymer
 4. Nanometric chromophoric particles (1-100 nm)
 5. Embedding material
 6. Product (packaging, goods, film, . . . )
 7. Reversible binding system displaceable by the analyte molecule
 8. Chemically reactive polymer after reaction with molecules from (11)
 9. Freezing-thawing process
 10. Micro/nanocapsules with reagent which reacts with (3) after bursting of the capsules
 11. Micro/nanocapsules (10) which have burst as a result of the freezing/thawing process and leaked
 12. The arrow shows the distance from particle surface (1) to nanometric chromophoric particles (4) which is important for the formation of the resonance color and which changes after the freezing/thawing process The bursting of the (nano)capsules results in release of a reagent that, after the next thawing process, chemically changes the nanostructure of the pigment, preferably the polymer layer itself, and produces a change in the color of the pigment thereby.

The invention claimed is:

1. A sensory pigment for use in foods, packaging, pharmaceutical products, paper and electronic products, which comprises metallic, metal-containing carrier particles (1) or carrier particles (1) containing at least one metal-oxygen compound, with a size of the longer particle axis greater than 300 nm, wherein the carrier particles (1) comprise at least one layer of chromophoric particles (4) having a size of from 1 to 100 nm, and interposed between the carrier particles (1) and the layer(s) of chromophoric particles (4), a 5 to 500 nm thick layer of at least one chemically reactive (bio)organic or inorganic polymer (3), wherein a reaction of the polymer to an external chemical or physical stimulus causes a structural change in the polymer layer (3), which results in a change, visible to the human eye or measurable in the infrared range, in a color of the pigment by resonance-amplified optical absorption.

2. The sensory pigment as claimed in claim 1, wherein the thickness of the polymer layer (3) changes in reaction to the chemical or physical stimulus.

3. The sensory pigment as claimed in claim 1, wherein the metallic, metal-containing carrier particles (1) or particles (1) containing at least one metal-oxygen compound have a lamellar or fibrous form.

4. The sensory pigment as claimed in claim 1, wherein the pigment further comprises an inert layer (2) of less than 500 nm thickness between the carrier particles (1) and the reactive polymer layer (3).

5. The sensory pigment as claimed in claim 1, wherein the pigment is mixed with a binder (5) which, optionally, is adhesive.

6. The sensory pigment as claimed in claim 5, wherein the binder (5) is a liquid formulation which can be printed, sprayed or spread on.

7. The sensory pigment as claimed in claim 1, wherein the carrier particles (1), the reactive polymer layer (3) and the layer(s) of chromophoric particles (4) are configured to give a color change to green or blue following reaction of the polymer layer (3) with a positive or desirable stimulus, or to give a color change to a red or yellow shade following reaction of the polymer layer (3) with a negative or undesirable stimulus.

8. The sensory pigment as claimed in claim 1, wherein the chromophoric particles (4) are in the form of nanoparticles and comprise metallic or strongly chromophoric particles.

9. The sensory pigment as claimed in claim 8, wherein the nanoparticles are particles of elements or compounds of elements selected from the group consisting of silver, gold, palladium, platinum, rhodium, copper, indium, aluminum, nickel, cobalt, chromium, iron, vanadium, molybdenum, tungsten, titanium, niobium, tantalum, zirconium, tin, germanium, bismuth, antimony, carbon and silicon, or alloys thereof, wherein the nanoparticles are optionally surrounded by corrosion-protecting capsules having a thickness of up to 100 nm.

10. The sensory pigment as claimed in claim 1, wherein the chromophoric particles (4) are in the form of nanoparticles and are selected from the group consisting of the anthraquinone pigments, quinacridone pigments, diketopyrrolopyrrole pigments, phthalocyanine pigments, azo pigments and isoindoline pigments, and are prepared from and/or contain anionic and cationic dyes, mordant dyes, disperse dyes, ingrain or coupling dyes, vat dyes, metal complex dyes, reactive dyes with particulate deposition and/or pigment dyes which acquire pigment properties through lacking a basic function on a sulfone, phosphate or carboxyl group.

11. The sensory pigment as claimed in claim 8, wherein the nanoparticles are applied between the carrier particles (1) and the reactive polymer layer (3), and the nanoparticles lead to a color enhancement and/or a color change.

12. The sensory pigment as claimed in claim 1, wherein the chemically reactive (bio)organic polymer is selected from the group consisting of proteins, polyamides, polyamines, polyglycosides and polyesters, and wherein the reaction is a chemical reaction selected from the group consisting of hydrolysis, oxidation, reduction, displacement of ligands by more strongly binding ones and a change in protonation or hydration.

13. The sensory pigment as claimed in claim 1, wherein the chemically reactive (bio)organic polymer comprises hydratable groups and the polymer layer (3) swells upon exposure to moisture.

14. The sensory pigment as claimed in claim 13, wherein the polymer comprising hydratable groups is selected from the group consisting of polyacrylates, polymethacrylates, poly-N-vinylpyrrolidones, polyvinyl alcohols, polyvinyl acetates, polyvinyl butyrates, polyamines and polyamines, or is a copolymer.

15. The sensory pigment as claimed in claim 5, wherein the pigment is embedded in the binder (5), and comprises a water-containing gel or a water-swellable or water-permeable layer, or is in the form of a porous matrix, the pore size of which allows an analyte to penetrate to the pigment.

16. The sensory pigment as claimed in 15, wherein the binder (5) is in the form of a porous matrix, and does not adhesively bond the nanoparticles so that they can be released after chemical reaction.

17. The sensory pigment as claimed in claim 6, wherein the binder (5) additionally comprises micro- or nanocapsules containing one or more reagents, wherein the micro- or nanocapsules change upon freezing so that, after rethawing, the one or more reagents are released and react irreversibly with the reactive polymer layer (3) causing a change in the color of the pigment.

18. The sensory pigment as claimed in 17, wherein the one or more reagents is selected from the group consisting of acids, alkalis, complexing agents, chemical crosslinking agents, oxidizing agents, reducing agents and enzymes.

19. A method of using the sensory pigment as claimed in claim 1 to provide smart color-variable surfaces and for the inscription thereof and/or for the representation of images or technical code, said method comprising applying the sensory pigment to a food, packaging, pharmaceutical product, paper or electronic product.

20. The method of claim 19, wherein the technical code is a barcode.

21. The method of claim 19, wherein the pigment is applied by inscribing with a substance selected from the group consisting of acids, alkalis, complexing agents, chemical crosslinking agents, oxidizing agents, reducing agents, precipitating agents, complexing agents and enzymes, or is applied with heat, light, electrical energy or magnetic energy.

22. The method of claim 19, wherein a color change, the representation of images or technical codes, or a representation of text can be cancelled by a chemical reaction, electromagnetic energy, or by the lapse of time.

23. The method of claim 22, wherein the chemical reaction comprises a chemical selected from the group consisting of acids, alkalis, water, drying agents, reducing agents, oxidizing agents, solvents and complexing agents.

24. The method of claim 22, wherein the electromagnetic energy is heat or a magnetic field.

25. The method of claim 19, wherein a color change is triggered in the color-variable surfaces by body contact.

26. The method of claim 19, wherein a color change is triggered in the color-variable surfaces by hand moisture and warmth.

27. The sensory pigment as claimed in claim 1, wherein the polymer layer (3) comprises more than one type of polymer.

28. The sensory pigment as claimed in claim 27, wherein the polymer layer (3) comprises cationic and anionic polymers bound alternately or biopolymers combined with organic polymers.

29. The sensory pigment as claimed in claim 28, wherein the biopolymers are proteins and/or polysugars and the organic polymers are hydrogels.

30. A process for preparing the sensory pigments of claim 1, comprising precipitating polymers onto particles or binding by a precipitation process via a solvent change or via a pH change of a polymer solution or by direct polymerization on the particle surface or by chemical crosslinking of dissolved polymers for binding thereof on the particle surface from monomers or low molecular weight prepolymers.

31. The process as claimed in claim 30, wherein the polymers are formed by in situ polymerization on the particle surface (1 or 2 or 3), an initiator molecule being bound to the surface and the polymerization starting directly from the surface.

32. The process as claimed in claim 31, wherein the polymerization processes uses living radicals.

* * * * *